US012233169B2

United States Patent
Neikirk

(10) Patent No.: US 12,233,169 B2
(45) Date of Patent: *Feb. 25, 2025

(54) VAPOR PHASE COATING TECHNOLOGY FOR PHARMACEUTICAL ABUSE DETERRENT FORMULATIONS

(71) Applicant: Applied Materials, Inc., Santa Clara, CA (US)

(72) Inventor: Colin C. Neikirk, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 17/004,827

(22) Filed: Aug. 27, 2020

(65) Prior Publication Data

US 2021/0059954 A1    Mar. 4, 2021

Related U.S. Application Data

(60) Provisional application No. 62/892,465, filed on Aug. 27, 2019.

(51) Int. Cl.
| | |
|---|---|
| A61K 9/51 | (2006.01) |
| B82Y 5/00 | (2011.01) |
| B82Y 30/00 | (2011.01) |
| B82Y 40/00 | (2011.01) |
| C23C 16/40 | (2006.01) |
| C23C 16/44 | (2006.01) |

(52) U.S. Cl.
CPC .......... *A61K 9/5192* (2013.01); *A61K 9/5115* (2013.01); *B82Y 5/00* (2013.01); *B82Y 30/00* (2013.01); *B82Y 40/00* (2013.01); *C23C 16/40* (2013.01); *C23C 16/4408* (2013.01)

(58) Field of Classification Search
CPC ............ B82Y 5/00; B82Y 30/00; B82Y 40/00
See application file for complete search history.

(56) References Cited

U.S. PATENT DOCUMENTS

| | | | |
|---|---|---|---|
| 6,165,512 A | 12/2000 | Mezaache et al. | |
| 6,613,383 B1 | 9/2003 | George et al. | |
| 8,524,772 B2 | 9/2013 | Arad et al. | |
| 9,700,515 B2 | 7/2017 | Odidi | |
| 2003/0026989 A1 | 2/2003 | George et al. | |
| 2003/0118642 A1 | 6/2003 | Norman et al. | |
| 2004/0037883 A1 | 2/2004 | Zhou et al. | |
| 2005/0266078 A1 | 12/2005 | Jorda et al. | |
| 2006/0263479 A1 | 11/2006 | Boghani et al. | |
| 2007/0036850 A1 | 2/2007 | Roehrich et al. | |
| 2008/0315293 A1* | 12/2008 | Ji .................. | H01L 29/40117 438/761 |
| 2009/0186968 A1 | 7/2009 | Zong et al. | |
| 2010/0297251 A1 | 11/2010 | Timmons et al. | |
| 2010/0303722 A1 | 12/2010 | Jin et al. | |
| 2011/0091563 A1 | 4/2011 | Kurasawa et al. | |
| 2011/0300224 A1 | 12/2011 | Murpani et al. | |
| 2012/0201860 A1 | 8/2012 | Weimer et al. | |
| 2013/0280177 A1* | 10/2013 | Raman ................. | A61K 9/2031 424/44 |
| 2013/0306927 A1* | 11/2013 | Marsh ................ | H10N 70/8828 423/276 |
| 2013/0336866 A1 | 12/2013 | Soeger et al. | |
| 2013/0337056 A1* | 12/2013 | Lehtonen ............. | A61K 9/2893 424/490 |
| 2015/0250731 A1 | 9/2015 | Hoppu et al. | |
| 2016/0081945 A1* | 3/2016 | Carlsson ............ | A61K 31/4422 424/490 |
| 2017/0007545 A1 | 1/2017 | Hoppu et al. | |
| 2019/0216742 A1* | 7/2019 | Neikirk ................. | C23C 16/458 |
| 2020/0197313 A1 | 6/2020 | Hoppu et al. | |

FOREIGN PATENT DOCUMENTS

| | | |
|---|---|---|
| DE | 10307568 | 9/2004 |
| EP | 1621187 | 2/2006 |
| JP | 2004269384 | 9/2004 |
| JP | 2005060309 | 3/2005 |
| JP | 2005520796 | 7/2005 |
| JP | 2008013480 | 1/2008 |
| JP | 2008539801 | 11/2008 |
| JP | 2010501538 | 1/2010 |

(Continued)

OTHER PUBLICATIONS

'www.ahdictionary.com' [online]. "granule," [retrieved on Aug. 9, 2019]. Retrieved from the Internet: <https:www.ahdictionary.com/word/search/html?q=granule>. 3 pages.

Knez et al., "Atomic Layer Deposition on Biological Macromolecules: Metal Oxide Coating of Tobacco Mosaic Virus and Ferritin," Nano Letters, 2006, 6(6):1172-7.

Martino et al., "A new pure paracetamol for direct compression: The orthorhombic form," International Journal of Pharmaceutics, 1996, 128: 1-8.

Patel et al., "Ensuring Better Control of Granulation", Pharmaceutical Manufacturing, Aug. 7, 2008, http://www.pharmamanufacturing/com/articles/2008/096/, 11 pages.

Pharmaceutical Preparations European Pharmacopoeia 8.0, Apr. 2013, 756-8.

Verheezen et al., "Milling of agglomerates in an impact mill," Int. J Pharm, 2004, 278:165-72.

Xie et al. "Atomic layer deposition of TiO2 from tetrakis-dimethyl-amido titanium or Ti isopropoxide precursors and H2O," Journal of Applied Physics, 2007, 102:7 pages.

(Continued)

*Primary Examiner* — Andrew S Rosenthal
(74) *Attorney, Agent, or Firm* — Fish & Richardson P.C.

(57) ABSTRACT

A method of preparing an abuse deterrent pharmaceutical composition having a drug-containing core enclosed by one or more metal oxide materials is provided. The method includes the sequential steps of (a) loading the particles comprising the drug into a reactor, (b) applying a vaporous or gaseous metal precursor to the particles in the reactor, (c) performing one or more pump-purge cycles of the reactor using inert gas, (d) applying a vaporous or gaseous oxidant to the particles in the reactor, and (e) performing one or more pump-purge cycles of the reactor using inert gas. This produces an abuse deterrent pharmaceutical composition comprising a drug containing core enclosed by one or more metal oxide materials.

27 Claims, 3 Drawing Sheets

(56) References Cited

FOREIGN PATENT DOCUMENTS

| | | |
|---|---|---|
| JP | 2012051810 | 3/2012 |
| JP | 2014510066 | 4/2014 |
| WO | WO 90/02546 | 3/1990 |
| WO | WO 2006/090640 | 8/2006 |
| WO | WO 2008/023184 | 2/2008 |
| WO | WO 2010/135107 | 11/2010 |
| WO | WO 2011/011207 | 1/2011 |
| WO | WO 2011/141486 | 11/2011 |
| WO | WO 2012/116814 | 9/2012 |

OTHER PUBLICATIONS

PCT International Search Report and Weitten Opinion in International Application No. PCT/US2020/048196, dated Dec. 2, 2020, 13 pages.

Office Action in IN Appln. No. 202247014973, dated Apr. 4, 2022, 6 pages.

U.S. Appl. No. 17/636,293, filed Sep. 22, 2022, Neikirk.

Extended European Search Report in European Appln. No. 20857873.2, dated Oct. 6, 2023, 10 pages.

Kääriäinen et al., "Surface modification of acetaminophen particles by atomic layer deposition," International Journal of Pharmaceutics, Jun. 15, 2017, 525(1):160-174.

\* cited by examiner

|  | Metal Precursor Dosing | Purge 1 | Oxidizer Dosing | Pump 2 |
|---|---|---|---|---|
| Fill Pressure | 0.1 Torr to 0.5 × $P_{saturation, Metal}$ | 1 Torr to 100 Torr | 0.1 Torr to 0.5 × $P_{saturation, Ox}$ | 1 Torr to 100 Torr |
| Hold Time | 1 s to 600 s | 1 s to 600 s | 1 s to 600 s | 1 s to 600 s |
| Pump Pressure | < 1 Torr (50 mTorr typical) | < 1 Torr (50 mTorr typical) | < 1 Torr (50 mTorr typical) | < 1 Torr (50 mTorr typical) |
| Number of Repeats | Determined by reactor volume, pressure, & powder surface area (1-10 typical) | 1 to 10 typical. Higher gives more ALD-like deposition. Lower gives more CVD. | Determined by reactor volume, pressure, & powder surface area (1-10 typical) | 1 to 10 typical. Higher gives more ALD-like deposition. Lower gives more CVD. |

FIG. 2

VAPOR PHASE COATING TECHNOLOGY FOR PHARMACEUTICAL ABUSE DETERRENT FORMULATIONS

CROSS-REFERENCE TO RELATED APPLICATIONS

This application claims priority to U.S. Provisional Patent Application Ser. No. 62/892,465, filed Aug. 27, 2019, the disclosure of which is incorporated by reference.

TECHNICAL FIELD

This disclosure pertains to pharmaceutical compositions and methods of preparing metal oxide encapsulated pharmaceuticals for abuse deterrence.

BACKGROUND

Existing abuse deterrent formulations (ADF) require many processing steps and the inclusion of large amounts of excipient materials which may interact negatively with the active pharmaceutical ingredient (API). ADF technologies utilize primarily wet phase coating or dry particle blending. Such process complexity adds significantly to their cost of manufacture, which is undesirable. More importantly, the excipients used to prevent drug abuse must not interfere with the actual pharmacological activity of the drug. This can be a large challenge as the excipients are specifically designed to, for instance, prevent dissolution.

SUMMARY

The present disclosure describes ADF technology that employs dry (vacuum/vapor phase) coating processes to deposit existing materials for ADFs. The technology may also enable coating of new materials of interest for ADF which are not amenable to coating by existing technologies.

The methods described herein enable thin, uniform, conformal, and dense coatings, regardless of particle size. These highly precise coatings can minimize the coating overburden required to provide effective abuse deterrent, thereby minimizing the risk of the deterrent formulation impacting pharmacological performance. Additionally, hybrid organic-inorganic coating structures can be prepared which enable new modes of abuse deterrence, combining both physical and chemical barriers in a single process.

This technology is intended to produce abuse deterrent pharmaceutical formulations through advanced vapor phase coating techniques. These coatings may be organic polymers, inorganic oxides, or some combination thereof. Coatings for ADF function by providing a physical or chemical barrier to drug dissolution or crushing to prevent various forms of dose loading, such as dissolution in alcohol, syringing, crushing, or chewing. Physical barriers may have a pH switching component to prevent dose loading by the consumer, without affecting pharmacokinetics in the body. Chemical barriers may also function as a pH solubility switch which, when used in combination with a pH modifying excipient, can prevent dissolution outside the body without affecting pharmacokinetics in the body. ADFs may also include an aversive component, which changes the texture, taste, or smell of the compound so as to make dose loading undesirable. For example, the aversive component may result in the formation of a highly viscous gel when the drug is dissolved which prevents it from being drawn into a syringe. Other mechanisms of abuse deterrence are also possible (such as agonist/antagonist pairs); however, this disclosure relates specifically to physical and chemical barriers and aversive coatings.

Metal oxide materials are coated through one or more of an atomic layer deposition (ALD) or chemical vapor deposition (CVD) process. Polymers are coated through one or more of a molecular layer deposition (MLD), initiated (hot filament) chemical vapor deposition (iCVD), or aerosol-assisted spray deposition process (AA-CVD). These technologies share the unique benefits of high coating uniformity, independent of particle size, with good conformal coverage and a relative lack of pinhole defects, and are amenable to a common reactor architecture, described elsewhere. The particles being coated are agitated (by rotation, gas flow, or vibration) during deposition to ensure high throughput and good uniformity.

ALD deposition of metal oxides takes place at temperatures from about room temperature to 300 C by alternating doses of precursors such as TMA or $TiCl_4$ and oxidizers such as water vapor or ozone. The superior chemical inertness and physical strength of metal oxides make them promising new candidates for ADFs. They may also show pH dependent solubility properties. In the coating process, precursors are dosed into a reactor in either static mode or flow-through mode. In static mode, reactants are pulsed into a closed reactor and allowed to dwell in the reactor until consumed. Reaction byproducts are then pumped out and the reactant is pulsed again until all reaction sites on the powder have been occupied. The reactor is then purged of residual reactant by a flow of an inert gas, which may or may not be heated or ionized to enhance efficiency of the purge. The cycle is then repeated with the second reactant. In flow-through mode, the flow rate of the reactant is set such that it is fully or nearly fully consumed in the reactor without closing the reactor exhaust. Organic polymer layers can be deposited in this reactor via either molecular layer deposition or initiated (hot filament) chemical vapor deposition (iCVD). MLD is an alternating process analogous to the process described for ALD above and can be used for the deposition of condensation polymers such as polyamides and polyesters, which may be branched or crosslinked. pH responsive polyesters or polyamides are commonly used in pharmaceutical enteric coatings and are also of interest for chemical and physical barrier based ADFs. Depending on their chemical formulation, they may also form gels for aversive formulations. In the MLD process, particles are coated by dosing alternating physisorbed or chemisorbed monolayers consisting of one or more complementary pairs of multifunctional Lewis acids and bases. The Lewis bases may consist of multifunctional alcohols such as diethylene glycol or amines such as ethylene diamine. The Lewis acids may consist of multifunctional acid chlorides such as succinyl chloride, glutaryl chloride, or adipoyl chloride. Trifunctional Lewis acids or bases such as trimesoyl chloride can be used to introduce branching or crosslinking. Hybrid organic-inorganic materials can also be prepared using a metal-organic precursor (such as TMA) as the Lewis acid. These alternating layers can be dosed in either static or flow through mode, as specified for ALD above.

An iCVD process can be used for the deposition of chain-growth polymers, such as poly (acrylates), poly (methacrylates), and poly (styrenes) and their copolymers. Among these materials, amino-esters of acrylic and methacrylic acid (such as pDMAEMA and pEMAEMA) in particular are commonly used in ADFs due to their pH dependent swelling behavior.

Additionally, hydrogel materials (such as crosslinked acrylamides) can show a high degree of swellability and are therefore prime candidates for aversive coatings. In the iCVD process, one or more monomer precursors chosen from the subset of vinyl, acrylate, methacrylate, acrylamide, methacrylamide, or styrene chemistries flow into the reactor through a vapor delivery system (i.e. bubbler or direct liquid injection) capable of delivering 1-100 g/min of monomer vapor. Copolymers can also be prepared by coinjection of multiple different monomers. A second injector provides delivery of a thermal initiator, such as an organic peroxide. The initiator flows over a heated element before entering the reactor. This heated element cracks the initiator to form two peroxy radicals without interacting with the monomer vapor. These radicals then induce chain growth polymerization of monomer species physically adsorbed on the surface of the particles to be coated.

These processes result in dense, conformal, highly uniform films, which cannot be produced by incumbent pharmaceutical coating processes today. These precision coatings can achieve good abuse deterrence while minimizing the coating's effect on pharmacological behavior. Furthermore, they can minimize excipient loadings by enabling identical performance in thinner coatings, allowing increased drug dosage in a smaller dosage form factor. Additionally, dense, continuous metal oxide coatings enabled by this technique are a new class of physical barriers which has not previously been explored. Finally, these processes can be used in combination to create laminate structures with multiple physical and chemical barriers, resulting in a unique combination of abuse deterrent properties that cannot be achieved using a single material alone.

In one aspect, a method of preparing a pharmaceutical composition having a drug-containing core enclosed by one or more metal oxide materials and having abuse deterrent properties is provided. The method includes the sequential steps of (a) loading the particles comprising the drug into a reactor, (b) applying a vaporous or gaseous metal precursor to the particles in the reactor, (c) performing one or more pump-purge cycles of the reactor using inert gas, (d) applying a vaporous or gaseous oxidant to the particles in the reactor, and (e) performing one or more pump-purge cycles of the reactor using inert gas. This produces a pharmaceutical composition comprising a drug containing core enclosed by one or more metal oxide materials.

Implementations may include one or more of the following features.

The sequential steps (b)-(e) may be repeated one or more times to increase the total thickness of the one or more metal oxide materials that enclose the core.

The reactor pressure may be allowed to stabilize following step (a), step (b), and/or step (d).

The reactor contents may be agitated prior to and/or during step (b), step (c), and/or step (e).

A subset of vapor or gaseous content may be pumped out prior to step (c) and/or step (e).

The metal oxide materials may have a thickness in range of 0.1 nm to 100 nm.

The particles may include a drug and one or more pharmaceutically acceptable excipients.

The particles may have a median particle size, on a volume average basis, between 0.1 μm and 1000 μm.

The pharmaceutical composition may be removed from the reactor and admixed with a pharmaceutically acceptable diluent or carrier.

The particles may consist essentially of the active pharmaceutical ingredient (API).

The API may be any drug subject to abuse, for example an opioid (oxycodone, naloxone, morphine, naltrexone, hydrocodone, sufentanil, oxymorphone, codeine, fentanyl, hydromorphone, and tapentadol).

The one or more metal oxide materials may include aluminum oxide, titanium oxide, iron oxide, gallium oxide, magnesium oxide, zinc oxide, niobium oxide, hafnium oxide, tantalum oxide, lanthanum oxide, and/or zirconium dioxide.

The one or more metal oxide materials may consist of aluminum oxide and/or titanium oxide.

The oxidant may be selected from the group of water, ozone, and organic peroxide.

In another aspect, a pharmaceutical composition having a drug-containing core enclosed by one or more metal oxide materials may be prepared by any of the above methods Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

BRIEF DESCRIPTION OF THE DRAWINGS

FIG. 2 is a table showing representative process conditions for the method.

DETAILED DESCRIPTION

Figure 1:
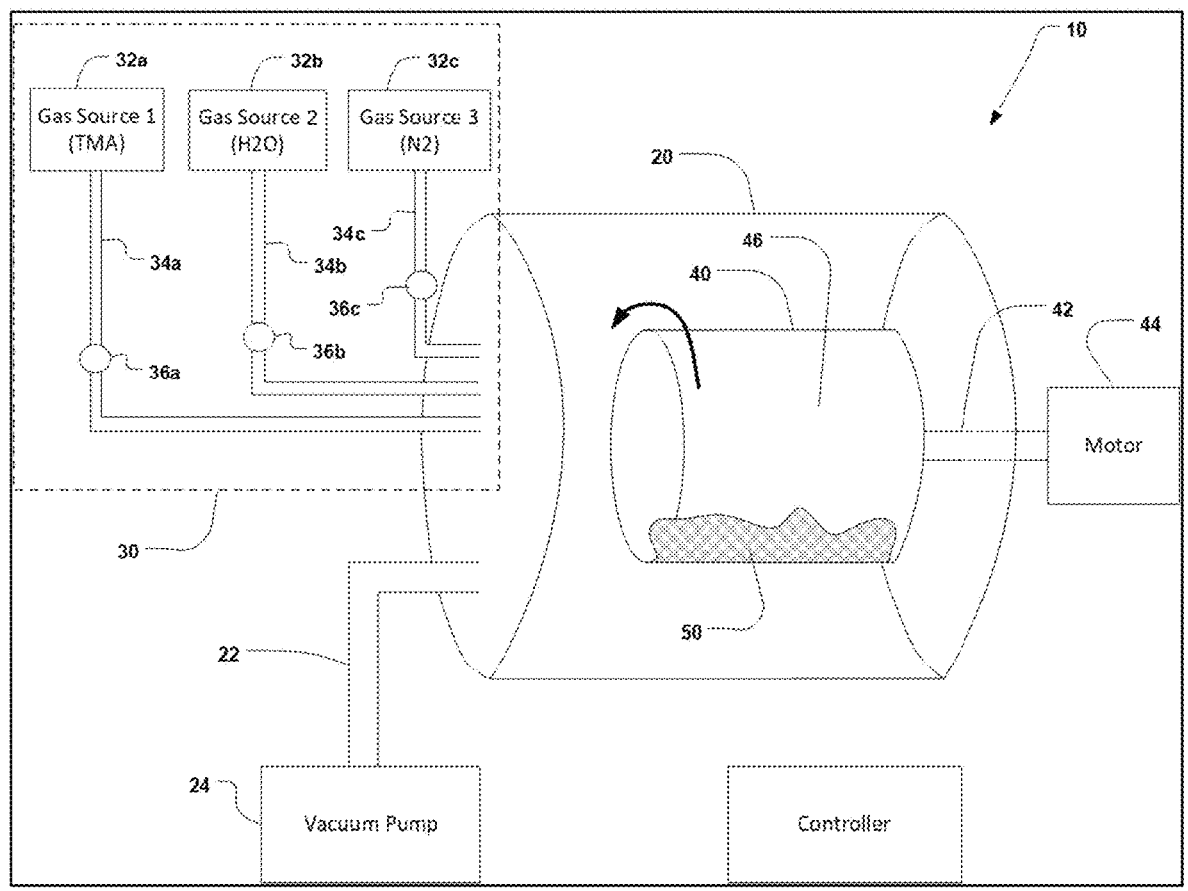
FIG. 1 is a schematic illustration of a rotary reactor for ALD and/or CVD coating of particles, e.g., drugs.

The present disclosure provides methods of preparing pharmaceutical compositions comprising drugs encapsulated by one or more layers of metal oxide. Such pharmaceutical compositions have abuse deterrent properties, for example, reduced crushability and/or reduced solubility. Overall, the provided methods of preparing the pharmaceutical compositions are able to safely, reliably, and predictably generate pharmaceutical compositions with the aforementioned properties. As result, the provided pharmaceutical compositions and methods of preparing metal oxide encapsulated drugs have increased therapeutic value, increased commercial value, and lower production cost per therapeutic dose.

The manufacture of the advantageous pharmaceutical compositions was enabled by the discovery that sequentially applying vaporous or gaseous metal precursor and vaporous or gaseous oxidant (and performing one or more pump-purge cycles using an inert gas after each application of said metal or oxidant). Preferably, the entire reaction takes place at 35° C. or below.

Herein are method is provided that utilizes a mechanical system and a chemical engineering process. The present disclosure also provides exemplary components and operating conditions of said system and process and exemplary drug substrates, vaporous and gaseous metal precursors, and vaporous and gaseous oxidants.

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Chemical Vapor Deposition (CVD)

Chemical vapor deposition is a thin-film deposition technique by which an element or chemical compound is deposited on a surface by chemical reaction in the gas phase or on a surface. It is distinct from atomic layer deposition in that the deposition is not self-limited, i.e., the film will continue to grow as long as chemistry is supplied. It is distinct from physical vapor deposition in that a chemical reaction results in a deposited film that is chemically different from the precursor species.

Reactor System

The term "reactor system" in its broadest sense includes all systems that could be used to perform ALD or mixed ALD/CVD or CVD. An exemplary reactor system is illustrated in FIG. 1 and further described below.

FIG. 1 illustrates a reactor system 10 for performing coating of particles, e.g., thermally sensitive particles, with thin-film coatings. The reactor system 10 can perform the coating using ALD and/or CVD coating conditions. The relative contribution of ALD and CVD processes to the thin-film coating can be controlled by appropriate selection of process conditions. In particular, the reactor system 10 permits a primarily ALD process, e.g., an almost entirely ALD process, to be performed at low processing temperature, e.g., below 50° C., e.g., at or below 35° C. For example, the reactor system 10 can form thin-film metal oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber (e.g., the chamber 20 and drum 40 discussed below) remain or be maintained at such temperatures.

Performing ALD reaction at low temperature conditions permits coatings to be formed on the particles without degradation of the biological components, e.g., the vaccine or bio-pharma ingredients. For example, a biological component in amorphous form can be coated without breaking down the biological component or converting the biological component to a crystalline form.

The reactor system 10 includes a stationary vacuum chamber 20 which is coupled to a vacuum pump 24 by vacuum tubing 22. The vacuum pump 24 can be an industrial vacuum pump sufficient to establish pressures less than 1 Torr, e.g., 1 to 100 mTorr, e.g., 50 mTorr. The vacuum pump 24 permits the chamber 20 to be maintained at a desired pressure, and permits removal of reaction byproducts and unreacted process gases.

In operation, the reactor 10 performs the ALD thin-film coating process by introducing gaseous precursors of the coating into the chamber 20. The gaseous precursors are spiked alternatively into the reactor. This permits the ALD process to be a solvent-free process. The half-reactions of the ALD process are self-limiting, which can provide Angstrom level control of deposition. In addition, the ALD reaction can be performed at low temperature conditions, such as below 50° C., e.g., below 35° C.

The chamber 20 is also coupled to a chemical delivery system 30. The chemical delivery system 30 includes three or more gas sources 32a, 32b, 32c coupled by respective delivery tubes 34a, 34b, 34c and controllable valves 36a, 36b, 36c to the vacuum chamber 20. The chemical delivery system 30 can include a combination of restrictors, gas flow controllers, pressure transducers, and ultrasonic flow meters to provide controllable flow rate of the various gasses into the chamber 20. The chemical delivery system 30 can also include one or more temperature control components, e.g., a heat exchanger, resistive heater, heat lamp, etc., to heat or cool the various gasses before they flow into the chamber 20. Although FIG. 1 illustrates separate gas lines extending in parallel to the chamber for each gas source, two or more of the gas lines could be joined, e.g., by one or more three-way valves, before the combined line reaches the chamber 20. In addition, although FIG. 1 illustrates three gas sources, the use of four gas sources could enable the in-situ formation of laminate structures having alternating layers of two different metal oxides.

Two of the gas sources provide two chemically different gaseous reactants for the coating process to the chamber 20. Suitable reactants include any of or a combination of the following: monomer vapor, metal-organics, metal halides, oxidants, such as ozone or water vapor, and polymer or nanoparticle aerosol (dry or wet). For example, the first gas source 32a can provide gaseous trimethylaluminum (TMA) or titanium tetrachloride ($TiCl_4$), whereas the second gas source 32b can provide water vapor.

One of the gas sources can provide a purge gas. In particular, the third gas source can provide a gas that is chemically inert to the reactants, the coating, and the particles being processed. For example, the purge gas can be N2, or a noble gas, such as argon.

A rotatable coating drum 40 is held inside the chamber 20. The drum 40 can be connected by a drive shaft 42 that extends through a sealed port in a side wall of the chamber 20 to a motor 44. The motor 44 can rotate the drum at speeds of 1 to 100 rpm. Alternatively, the drum can be directly connected to a vacuum source through a rotary union.

The particles to be coated, shown as a particle bed 50, are placed in an interior volume 46 of the drum 40. The drum 40 and chamber 20 can include sealable ports (not illustrated) to permit the particles to be placed into and removed from the drum 40.

The body of the drum 40 is provided by one or more of a porous material, a solid metal, and a perforated metal. The pores through the cylindrical side walls of the drum 40 can have a dimension of 10 μm.

In operation, one of the gasses flows into chamber 20 from the chemical delivery system 30 as the drum 40 rotates. A combination of pores (1-100 μm), holes (0.1-10 mm), or large openings in the coating drum serve to confine the particles in the coating drum while allowing rapid delivery of precursor chemistry and pumping of byproducts or unreacted species. Due to the pores in the drum 40, the gas can flow between the exterior of the drum 40, i.e., the reactor chamber 20, and the interior of the drum 40. In addition, rotation of the drum 40 agitates the particles to keep them separate, ensuring a large surface area of the particles remains exposed. This permits fast, uniform interaction of the particle surface with the process gas.

In some implementations, one or more temperature control components are integrated into the drum 40 to permit control of the temperature of the drum 40. For example, resistive heater, a thermoelectric cooler, or other component can in or on the side walls of the drum 40.

The reactor system 10 also includes a controller 60 coupled to the various controllable components, e.g., vacuum pump 24, gas distribution system 30, motor 44, a temperature control system, etc., to control operation of the reactor system 10. The controller 60 can also be coupled to various sensors, e.g., pressure sensors, flow meters, etc., to provide closed loop control of the pressure of the gasses in the chamber 20.

In general, the controller 60 can operate the reactor system 10 in accord with a "recipe." The recipe specifies an operating value for each controllable element as a function of time. For example, the recipe can specify the times during which the vacuum pump 24 is to operate, the times of and flow rate for each gas source 32a, 32b, 32c, the rotation rate of the motor 44, etc. The controller 60 can receive the recipe as computer-readable data (e.g., that is stored on a non-transitory computer readable medium).

The controller 60 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 60 is a general purpose programmable computer. In some implementations, the controller can be implemented using special purpose logic circuitry, e.g., an FPGA (field programmable gate array) or an ASIC (application specific integrated circuit).

Operation

Initially, particles are loaded into the drum 40 in the reactor system 10. The particles can have a solid core comprising a drug, e.g., one of the drugs discussed above. Once any access ports are sealed, the controller 60 operates the reactor system 10 according to the recipe in order to form the thin-film metal oxide layers on the particles.

In particular, the two reactant gases are alternately supplied to the chamber 20, with each step of supplying a reactant gas followed by a purge cycle in which the inert gas is supplied to the chamber 20 to force out the reactant gas and by-products used in the prior step. Moreover, one or more of the gases (e.g., the reactant gases and/or the inert gas) can be supplied in pulses in which the chamber 20 is filled with the gas to a specified pressure, a delay time is permitted to pass, and the chamber is evacuated by the vacuum pump 24 before the next pulse commences.

In particular, the controller 60 can operate the reactor system 10 as follows.

In a first reactant half-cycle, while the motor 44 rotates the drum 40 to agitate the particles 50:

i) The gas distribution system 30 is operated to flow the first reactant gas, e.g., TMA, from the source 32a into the chamber 20 until a first specified pressure is achieved. The specified pressure can be 0.1 Torr to half of the saturation pressure of the reactant gas.

ii) Flow of the first reactant is halted, and a specified delay time is permitted to pass, e.g., as measured by a timer in the controller. This permits the first reactant to flow through the particle bed in the drum 40 and react with the surface of the particles 50 inside the drum 40.

iii) The vacuum pump 50 evacuates the chamber 20, e.g., down to pressures below 1 Torr, e.g., to 1 to 100 mTorr, e.g., 50 mTorr.

These steps (i)-(iii) can be repeated a number of times set by the recipe, e.g., two to ten times, e.g., six times.

Next, in a first purge cycle, while the motor 44 rotates the drum to agitate the particles 50:

iv) The gas distribution system 30 is operated to flow the inert gas, e.g., N2, from the source 32c into the chamber 20 until a second specified pressure is achieved. The second specified pressure can be 1 to 100 Torr.

v) Flow of the inert gas is halted, and a specified delay time is permitted to pass, e.g., as measured by the timer in the controller. This permits the inert gas to flow through the pores in the drum 40 and diffuse through the particles 50 to displace the reactant gas and any vaporous by-products.

vi) The vacuum pump 50 evacuates the chamber 20, e.g., down to pressures below 1 Torr, e.g., to 1 to 500 mTorr, e.g., 50 mTorr.

These steps (iv)-(vi) can be repeated a number of times set by the recipe, e.g., six to twenty times, e.g., sixteen times.

In a second reactant half-cycle, while the motor 44 rotates the drum 40 to agitate the particles 50:

vii) The gas distribution system 30 is operated to flow the second reactant gas, e.g., H2O, from the source 32b into the chamber 20 until a third specified pressure is achieved. The third pressure can be 0.1 Torr to half of the saturation pressure of the reactant gas.

viii) Flow of the second reactant is halted, and a specified delay time is permitted to pass, e.g., as measured by the timer in the controller. This permits the second reactant to flow through the pores in the drum 40 and react with the surface of the particles 50 inside the drum 40.

ix) The vacuum pump 50 evacuates the chamber 20, e.g., down to pressures below 1 Torr, e.g., to 1 to 500 mTorr, e.g., 50 mTorr.

These steps (vii)-(ix) can be repeated a number of times set by the recipe, e.g., two to ten times, e.g., six times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

As noted above, the coating process can be performed at low processing temperature, e.g., below 50° C., e.g., at or below 35° C. In particular, the particles can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles.

In addition, physical components of the chamber can remain or be maintained at such temperatures, e.g., using a cooling system, e.g., a thermoelectric cooler, if necessary.

Process for Preparing Pharmaceutical Compositions Comprising Drugs Encapsulated by One or More Layers of Metal Oxide Provided are two exemplary methods for a pharmaceutical composition comprising a drug-containing core enclosed by one or more metal oxide materials. The first exemplary method includes the sequential steps of: (a) loading the particles comprising the drug into a reactor, (b) applying a vaporous or gaseous metal precursor to the substrate in the reactor, (c) performing one or more pump-purge cycles of the reactor using inert gas, (d) applying a vaporous or gaseous oxidant to the substrate in the reactor, and (e) performing one or more pump-purge cycles of the reactor using inert gas. While performing the method the temperature of the particles does not exceed 35° C.

In some embodiments of the first exemplary method, the sequential steps (b)-(e) are optionally repeated one or more times to increase the total thickness of the one or more metal oxide materials that enclose the solid core of the coated particles. In some embodiments, the reactor pressure is allowed to stabilize following step (a), step (b), and/or step (d). In some embodiments, the reactor contents are agitated prior to and/or during step (b), step (c), and/or step (e). In some embodiments, a subset of vapor or gaseous content is pumped out prior to step (c) and/or step (e).

The second exemplary method includes (e.g., consists of) the sequential steps of (a) loading the particles comprising the drug into a reactor, (b) reducing the reactor pressure to less than 1 Torr, (c) agitating the reactor contents until the reactor contents have a desired moisture content, (d) pressurizing the reactor to at least 10 Torr by adding a vaporous or gaseous metal precursor, (e) allowing the reactor pressure to stabilize, (f) agitating the reactor contents, (g) pumping out a subset of vapor or gaseous content and determining when to stop pumping based on analysis of content in reactor including metal precursor and byproduct of metal precursor reacting with exposed hydroxyl residues on substrate or on particle surface, (h) performing a sequence of pump-purge cycles of the reactor using inert gas, (i) pressuring the reactor to at least 10 Torr by adding a vaporous or gaseous oxidant, (j) allowing the reactor pressure to stabilize, (k) agitating the reactor contents, (l) pumping out a subset of vapor or gaseous content and determining when to stop pumping based on analysis of content in reactor including metal precursor, byproduct of metal precursor reacting with exposed hydroxyl residues on substrate or on particle surface, and unreacted oxidant, and (m) performing a sequence of pump-purge cycles of the reactor using inert gas.

In some embodiments of the second exemplary method, the sequential steps (b)-(m) are optionally repeated one or more times to increase the total thickness of the one or more metal oxide materials that enclose the solid core of the coated particles.

Pharmaceutically Acceptable Excipients, Diluents, and Carriers

Pharmaceutically acceptable excipients include, but are not limited to:
(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;
(2) binding agents such as cellulose, cross-linked polyvinylpyrrolidone, microcrystalline cellulose;
(3) filling agents such as lactose monohydrate, lactose anhydrous, microcrystalline cellulose and various starches;
(4) lubricating agents such as agents that act on the flowability of a powder to be compressed, including colloidal silicon dioxide, talc, stearic acid, magnesium stearate, calcium stearate, silica gel;
(5) sweeteners such as any natural or artificial sweetener including sucrose, xylitol, sodium saccharin, cyclamate, aspartame, and acesulfame K;
(6) flavoring agents;
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;
(8) buffers;
(9) Diluents such as pharmaceutically acceptable inert fillers, such as microcrystalline cellulose, lactose, dibasic calcium phosphate, saccharides, and/or mixtures of any of the foregoing;
(10) wetting agents such as corn starch, potato starch, maize starch, and modified starches, and mixtures thereof;
(11) disintegrants; such as croscarmellose sodium, crospovidone, sodium starch glycolate; and
(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate).

EXAMPLES

The following materials and methods were used in the Examples set forth herein.

Example 1: Prepare Particles Comprising Drug Encapsulated by Uniform, Thin Layers of Aluminum Oxide Coating with Nanometer Level Precision In this Example, one of the methods disclosed for preparing metal oxide encapsulated drugs is performed and the data is presented. In this Example, the vaporous or gaseous metal precursor is tri-methyl aluminum (TMA), the byproduct gaseous methane is formed after TMA reacts with exposed hydroxyl groups on the particles or on surface of the coated particles, and the oxidant is water vapor.

Method
In brief, the method comprised the sequential steps of:
(a) loading particles comprising the drug into a reactor;
(b) reducing the reactor pressure to less than 1 Torr;
(c) agitating the reactor contents until the reactor contents has a desired water content by performing residual gas analysis (RGA) to monitor levels of water vapor in the reactor;
(d) pressurizing the reactor to at least 1 Torr by adding a vaporous or gaseous TMA;
(e) allowing the reactor pressure to stabilize;
(f) agitating the reactor contents;

(g) pumping out a subset of vapor or gaseous content, including gaseous methane and unreacted TMA, and determining when to stop pumping by performing RGA to monitor levels of gaseous methane and unreacted TMA in the reactor.

(h) performing a sequence of pump-purge cycles on the reactor using nitrogen gas;

(i) pressuring the reactor to at least 1 Torr by adding water vapor;

(j) allowing the reactor pressure to stabilize;

(k) agitating the reactor contents;

(l) pumping out a subset of vapor or gaseous content, including water vapor, and determining when to stop pumping by performing RGA to monitor levels of water vapor in the reactor;

(m) performing a sequence of pump-purge cycles on the reactor using nitrogen gas.

While performing the method the internal reactor temperature did not exceed 35° C. Additionally, the steps of (b)-(m) were repeated more than once to increase the total thickness of the aluminum oxide that enclose said solid core. FIG. 2 includes representative process conditions for performing this method.

Results

Figure 3:
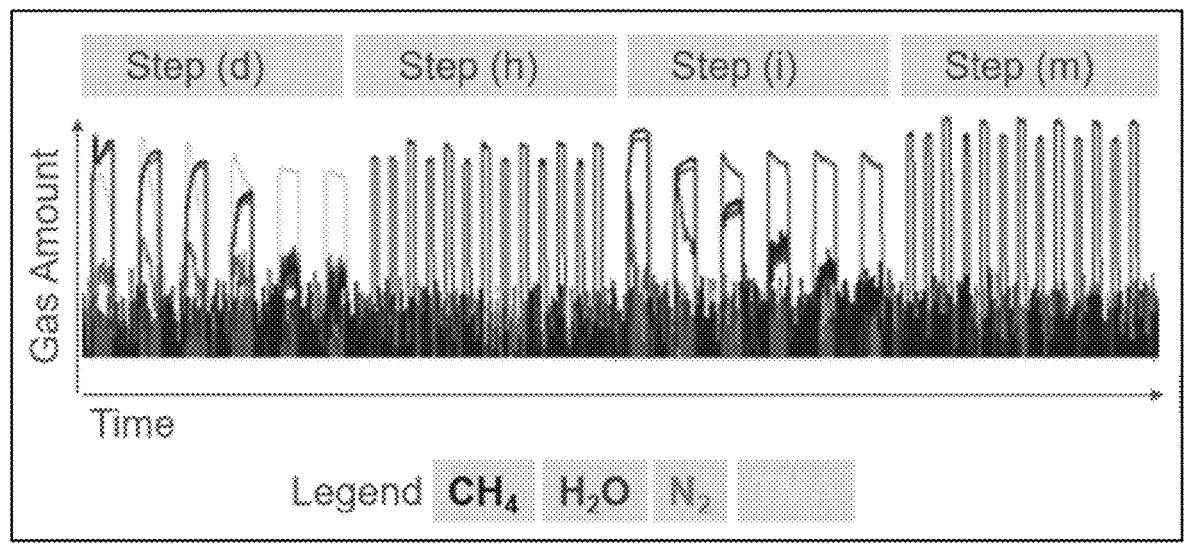
FIG. 3 is a graph depicting representative residual gas analysis traces measuring during steps (d), (h), (i), and (m) for one cycle of the method.

FIG. 3 shows representative residual gas analysis traces measuring during steps (d), (h), (i), and (m) for one cycle of the method. This method reproducibly shows growth rates between 2 and 4 angstroms of metal oxide coating per cycle. In contrast, a different method that limits growth to ALD only exhibited average growth per cycle of 1 angstroms per cycle. Without wishing to be bound to a particular theory, given the observed growth rate for this method the growth may be mediated by a combination of ALD and CVD.

What is claimed is:

1. A method of preparing an abuse deterrent pharmaceutical composition comprising opioid-containing particles enclosed by a combination of thin, conformal organic polymer and metal oxide coatings, the method comprising the sequential steps of:
   (a) loading the opioid-containing particles into a reactor;
   (b) applying a vaporous or gaseous metal oxide precursor to the opioid-containing particles in the reactor;
   (c) performing six or more pump-purge cycles of the reactor using inert gas, wherein each cycle comprises flowing an inert gas into the reactor to a pressure of 1-100 torr and after a delay time evacuating the reactor to reduce the pressure of the inert gas to below 1 torr;
   (d) applying a vaporous or gaseous oxidant to the opioid-containing particles in the reactor;
   (e) performing six or more pump-purge cycles of the reactor using inert gas, wherein each cycle comprises flowing an inert gas into the reactor to a pressure of 1-100 torr and after a delay time evacuating the reactor to reduce the pressure of the inert gas to below 1 torr; and
   (f) applying an organic polymer coating through initiated (hot filament) chemical vapor deposition (iCVD) or aerosol-assisted spray deposition process (AA-CVD), wherein the organic polymer comprises poly (acrylates), poly (methacrylates), poly (styrenes), or cross-linked polyacrylamides,
   thereby producing an abuse deterrent pharmaceutical composition comprising a opioid-containing particles enclosed by a combination of thin, conformal organic polymer and metal oxide coatings, wherein the coatings reduce the solubility and the crushability of the opioid-containing particles, wherein the temperature of the particles remains below 50° C., wherein the opioid-containing particles have a median particle size, on a volume average basis, of less than 10 microns, wherein the oxidant is water.

2. The method of claim 1, wherein the sequential steps (b)-(e) are repeated one or more times to increase the total thickness of the layer comprising one or more metal oxide materials that enclose the opioid-containing particles.

3. The method of claim 1, wherein the reactor pressure is allowed to stabilize following step (a), step (b), and/or step (d).

4. The method of claim 1, wherein the reactor contents are agitated prior to and/or during step (b), step (c), and/or step (e).

5. The method of claim 1, wherein a subset of vapor or gaseous content is pumped out prior to step (c) and/or step (e).

6. The method of claim 1, wherein the metal oxide layer has a thickness in range of 0.1 nm to 100 nm.

7. The method of claim 1, wherein the opioid-containing particles comprise one or more pharmaceutically acceptable excipients.

8. The method of claim 1, wherein the opioid-containing particles have a median particle size, on a volume average basis between 0.1 μm and 1000 μm.

9. The method of claim 1, wherein the pharmaceutical composition is removed from the reactor and admixed with a pharmaceutically acceptable diluent or carrier.

10. The method of claim 1, wherein the opioid-containing particles consist essentially of an opioid.

11. An abuse deterrent pharmaceutical composition comprising opioid-containing particles enclosed by a combination of thin, conformal organic polymer and metal oxide coatings, the method comprising the sequential steps of:
   (a) loading opioid-containing particles into a reactor;
   (b) applying a vaporous or gaseous metal precursor to the opioid-containing particles in the reactor;
   (c) performing six or more pump-purge cycles of the reactor using inert gas, wherein each cycle comprises a step of reducing the pressure of the inert gas to below 1 torr;
   (d) applying a vaporous or gaseous oxidant to the opioid-containing particles in the reactor;
   (e) performing six or more pump-purge cycles of the reactor using inert gas, wherein each cycle comprises a step of reducing the pressure of the inert gas to below 1 torr; and
   (f) applying an organic polymer coating through initiated (hot filament) chemical vapor deposition (iCVD) or aerosol-assisted spray deposition process (AA-CVD), wherein the organic polymer comprises poly (acrylates), poly (methacrylates), poly (styrenes), or cross-linked polyacrylamides,
   thereby producing an abuse deterrent pharmaceutical composition comprising opioid-containing particles enclosed by a combination of thin, conformal organic polymer and metal oxide coatings, wherein the coatings reduce the solubility and the crushability of the opioid-containing particles, wherein the temperature of the particles remains below 50° C., wherein the opioid-containing particles have a median particle size, on a volume average basis, of less than 10 microns, wherein the oxidant is water.

12. The composition of claim 11, wherein the sequential steps (b)-(e) are repeated one or more times to increase the total thickness of the one or more metal oxide materials that enclose the opioid-containing particles.

13. The composition of claim 11, wherein the reactor pressure is allowed to stabilize following step (a), step (b), and/or step (d).

14. The composition of claim 11, wherein the reactor contents are agitated prior and/or during to step (b), step (c), and/or step (e).

15. The composition of claim 11, wherein a subset of vapor or gaseous content is pumped out prior to step (c) and/or step (e).

16. The composition of claim 11, wherein the metal oxide layer has a thickness in range of 0.1 nm to 100 nm.

17. The composition of claim 11, wherein the opioid-containing particles comprise one or more pharmaceutically acceptable excipients.

18. The composition of claim 11, wherein the opioid-containing particles have a median particle size, on a volume average basis between 0.1 μm and 1000 μm.

19. The composition of claim 11, wherein the pharmaceutical composition is removed from the reactor and admixed with a pharmaceutically acceptable diluent or carrier.

20. The composition of claim 11, wherein the opioid-containing particles consist essentially of an opioid.

21. The composition of claim 11, wherein the drug is a small molecule, virus particle, polypeptide, polynucleotide, a composition comprising polypeptide and lipid, or a composition comprising polynucleotide and lipid.

22. The method of claim 1, wherein the layer is less than 200 nanometers thick.

23. The method of claim 1, wherein the layer is less than 100 nanometers thick.

24. The method of claim 1, wherein the layer is less than 50 nanometers thick.

25. The method of claim 1, wherein the layer is less than 10 nanometers thick.

26. The method of claim 1, wherein the opioid-containing particles have a median particle size, on a volume average basis, of less than 1 micron.

27. The method of claim 1, wherein the opioid-containing particles have a median particle size, on a volume average basis, of less than 100 nanometers.

\* \* \* \* \*